(12) United States Patent
Ikadai

(10) Patent No.: US 7,431,718 B2
(45) Date of Patent: *Oct. 7, 2008

(54) SKIN CARE DEVICE FOR TAKING OUT AND REMOVING SEBUM OR OTHER CUTANEOUS IMPURITIES

(75) Inventor: Kazuyasu Ikadai, Osaka (JP)

(73) Assignee: Matsushita Electric Works, Ltd., Osaka (JP)

( * ) Notice: Subject to any disclaimer, the term of this patent is extended or adjusted under 35 U.S.C. 154(b) by 170 days.

This patent is subject to a terminal disclaimer.

(21) Appl. No.: 11/037,251

(22) Filed: Jan. 19, 2005

(65) Prior Publication Data

US 2005/0159761 A1 Jul. 21, 2005

(30) Foreign Application Priority Data

Jan. 19, 2004 (JP) ............................. 2004-011099

(51) Int. Cl.
*A61M 1/00* (2006.01)
*A61M 35/00* (2006.01)
*A61H 7/00* (2006.01)
*A61H 9/00* (2006.01)
*A61B 17/50* (2006.01)

(52) U.S. Cl. ................. 604/540; 604/310; 604/313; 604/315; 608/131; 601/6; 601/159; 601/161

(58) Field of Classification Search ......... 604/289–316, 604/504; 606/131; 601/6, 7, 10, 12, 154, 601/159–161; 132/218, 317, 320
See application file for complete search history.

(56) References Cited

U.S. PATENT DOCUMENTS

| 2,710,114 | A | * | 6/1955 | Waber et al. ................. 221/232 |
| 6,309,364 | B1 | * | 10/2001 | Cathaud et al. ................ 601/7 |
| 6,319,211 | B1 | * | 11/2001 | Ito et al. ......................... 601/7 |
| 6,468,235 | B2 | * | 10/2002 | Ito et al. ......................... 601/6 |
| 2005/0159684 | A1 | * | 7/2005 | Ikadai ............................ 601/6 |
| 2005/0159760 | A1 | * | 7/2005 | Ikadai et al. ................. 606/131 |

FOREIGN PATENT DOCUMENTS

| EP | 0997156 | 5/2000 |
| JP | 53004648 | 1/1978 |
| JP | 2001-161438 | 6/2001 |

* cited by examiner

*Primary Examiner*—T. Zalukaeva
*Assistant Examiner*—Michael G Bogart
(74) *Attorney, Agent, or Firm*—Bacon & Thomas, PLLC

(57) ABSTRACT

A skin care device includes a suction nozzle to be brought into contact with skin to suction skin impurities therefrom, a suction pump for generating a suction force of the suction nozzle, a mist nozzle installed near the suction nozzle, for ejecting a mist of liquid, a tank for storing therein a liquid to be supplied to the mist nozzle, a liquid supply pump for supplying the liquid to the mist nozzle from the tank, a drive motor for driving the suction pump and the liquid supply pump at the same time, and a liquid amount control unit for controlling an amount of the liquid ejected from the mist nozzle. The liquid amount control unit is a flow rate regulation device disposed between the tank and the mist nozzle.

14 Claims, 10 Drawing Sheets

SKIN CARE DEVICE FOR TAKING OUT AND REMOVING SEBUM OR OTHER CUTANEOUS IMPURITIES

FIELD OF THE INVENTION

The present invention relates to skin care devices; and more particularly, to a skin care device for taking out and removing sebum and other cutaneous impurities from user's skin with a suction nozzle placed against the skin, while the contact between the suction nozzle tip and the skin is improved by spraying liquid onto the skin around the suction nozzle tip, thereby enhancing the skin care effect.

BACKGROUND OF THE INVENTION

A conventional skin care device treats user's skin with a suction nozzle, which is placed against the skin so that the tip of the suction nozzle touches and covers the skin. When a suction pump of the skin care device is then operated, the tip of the suction nozzle takes out and removes sebum and other cutaneous impurities from the skin (hereinafter, referred to as "skin impurities") while massaging the skin. Further, Japanese Patent Laid-open Publication No. 2001-161438 discloses a skin care device which sprays liquid onto the user's skin around the tip of a suction nozzle before or after a sebum suction treatment. Liquid sprayed before the sebum suction treatment helps the tip of the suction nozzle of the skin care device to slide smoothly on the skin, thereby allowing the skin care device easier to maneuver. Further, liquid sprayed after sebum suction treatment helps the irritated skin to be soothed and the skin pores to be closed.

Such a conventional skin care device has a feature which sprays a mist of the liquid by the Venturi effect in which air is pumped through an opening of a suction nozzle and a liquid from a tank is suctioned up under a negative pressure generated at a liquid supply side of the opening. By ejecting the mist of the liquid onto the skin before or after the skin treatment, sliding of the suction nozzle against the skin surface can be facilitated while the skin stays moisturized. However, in order to generate the mist of liquid from the Venturi effect, the air velocity needs to be raised, thereby increasing the amount of liquid mixed with the air flow at the same time. As a result, too much liquid supplied to the skin at once would drip down the user's face, which can be annoying to the user. Further, the mist spraying function cannot continue for a long time because the liquid is used up too fast.

It is preferable to supply a liquid to the skin constantly during a treatment so as to keep the skin lubricated and also to improve the contacting between the suction port nozzle and the skin. In case of the conventional skin care device, however, since a single pump serves as both a suction pump and a liquid supply pump, the mist ejecting operation and the suctioning operation cannot be performed at the same time. As a result, adequately firm contacting is not established between the suction port and the skin, thus failing to remove skin impurities effectively.

SUMMARY OF THE INVENTION

It is, therefore, an object of the present invention to provide a skin care device capable of performing a suctioning operation and a mist spraying operation at the same time; extending the mist spraying operation for a longer period while controlling the sprayed amount of a liquid properly without causing a discomfort to a user; and removing skin impurities sufficiently by allowing a firm contact to be established between the skin and a suction port.

In accordance with the present invention, there is provided a skin care device including: a suction nozzle to be brought into contact with skin to suction skin impurities therefrom; a suction pump for generating a suction force of the suction nozzle; a mist nozzle installed near the suction nozzle, for ejecting a mist of liquid; a tank for storing therein a liquid to be supplied into the mist nozzle; a liquid supply pump for supplying the liquid into the mist nozzle from the tank; a drive motor for driving the suction pump and the liquid supply pump at the same time; and a liquid amount control unit for controlling an amount of the liquid ejected from the mist nozzle.

BRIEF DESCRIPTION OF THE DRAWINGS

The above and other objects and features of the present invention will become apparent from the following description of preferred embodiments given in conjunction with the accompanying drawings, in which:

FIG. 5A offers a plan sectional view showing a cartridge of the flow rate regulation unit secured to the skin care device while

DETAILED DESCRIPTION OF THE PREFERRED EMBODIMENTS

Figure 1:
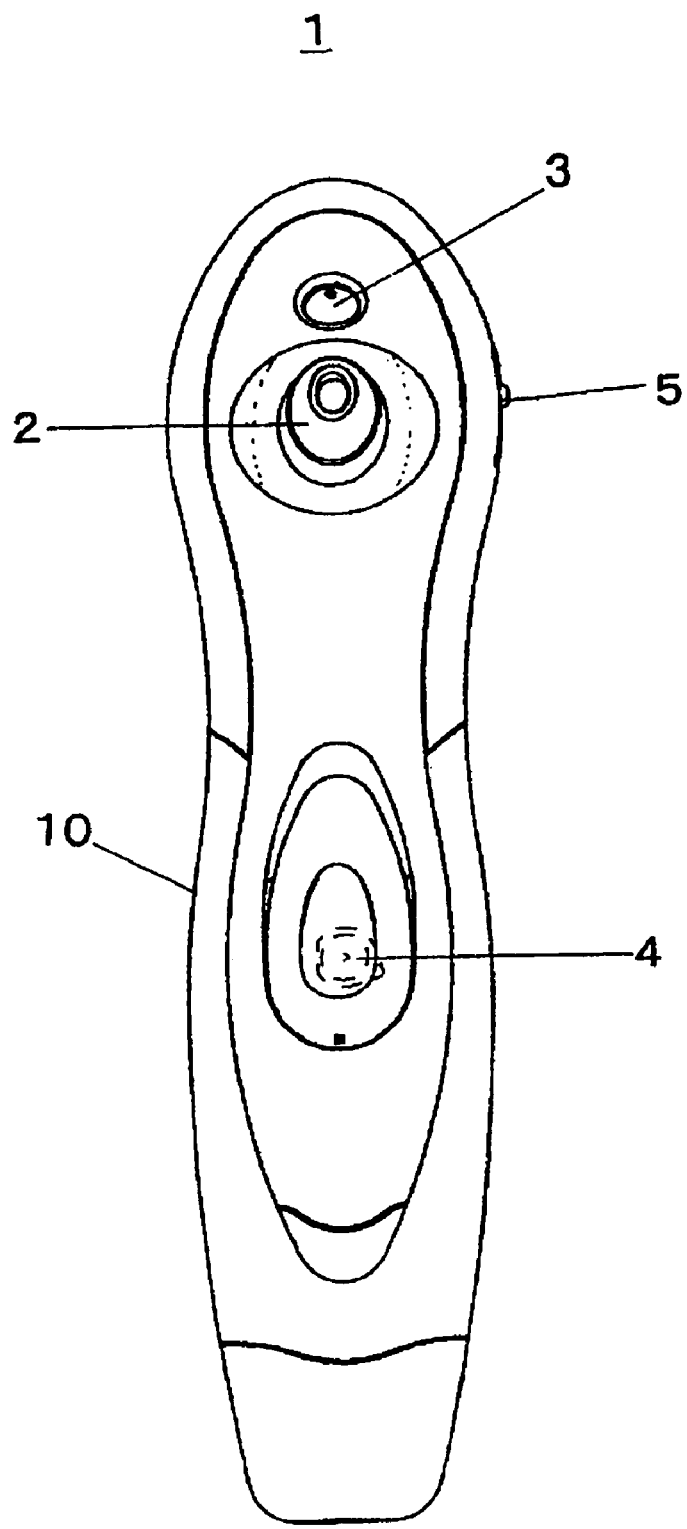
FIG. 1 is a front view of an appearance of a skin care device in accordance with a preferred embodiment of the present invention.

A preferred embodiment of the present invention will be described hereinafter with reference to the accompanying drawings. FIG. 1 is a front view of an appearance of a skin care device 1 in accordance with the preferred embodiment of the present invention and FIG. 2 sets forth a side sectional view showing the internal configuration thereof.

As shown in FIG. 1, an approximately lower half of a housing 10 of the skin care device 1 is a grip portion for allowing a user to hold the device 1. Further, a suction nozzle 2 is installed at an approximately central portion of the upper half of the housing 10 and a mist nozzle 3 for spraying a mist of a liquid toward skin is provided at a position near and above the suction nozzle 2. A main switch 4 for turning on and off the skin care device 1's suctioning operation for suctioning skin impurities is installed at an about central region of a front surface of the housing 10. Further, a mist control switch 5 for turning on and off the liquid ejecting operation is provided at an upper right lateral surface of the housing 10.

Figure 2:
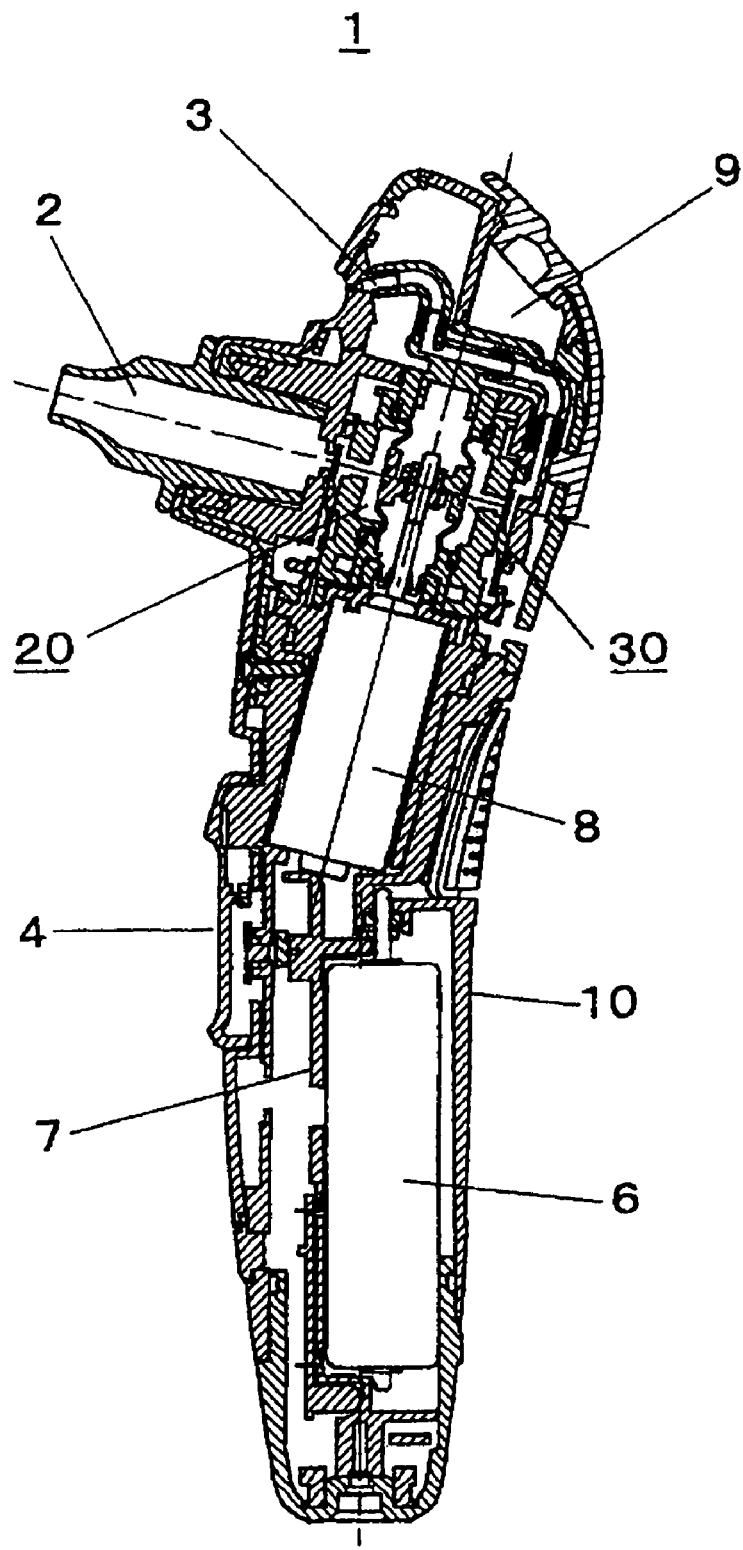
FIG. 2 provides a side sectional view showing an internal configuration of the skin care device.

As can be seen from FIG. 2, incorporated in the grip portion of the housing 10 are a battery 6 such as a rechargeable secondary battery, which serves a power supply of the skin care device 1, a contact terminal 7 of the main switch 4, and so forth. Further, a drive motor 8 is installed at an approximately central portion inside the housing 10, and both a suction pump 20 and a liquid supply pump 30 are disposed above the drive motor 8 and behind the suction nozzle 2, when viewed from the front, to face each other with a rotating shaft 81 interposed therebetween. Further, a tank 9 for storing therein a liquid such as water is disposed above the liquid supply pump 30. The suction nozzle 2 is configured as an attachment capable of being detachably secured to the suction pump 20.

The skin care device 1 in accordance with the preferred embodiment of the present invention is configured to drive the suction pump 20 and the liquid supply pump 30 simultaneously by using the single drive motor 8. As a result, the suctioning of skin impurities by the suction nozzle 2 and the ejection of liquid by the mist nozzle 3 can be performed at the same time. Moreover, with the employment of the configuration for driving the two pumps 20 and 30 by means of the single drive motor 8, the housing 10 can be reduced in its size with an improved weight balance while making easier to maneuver the skin care device 1.

Figure 3:
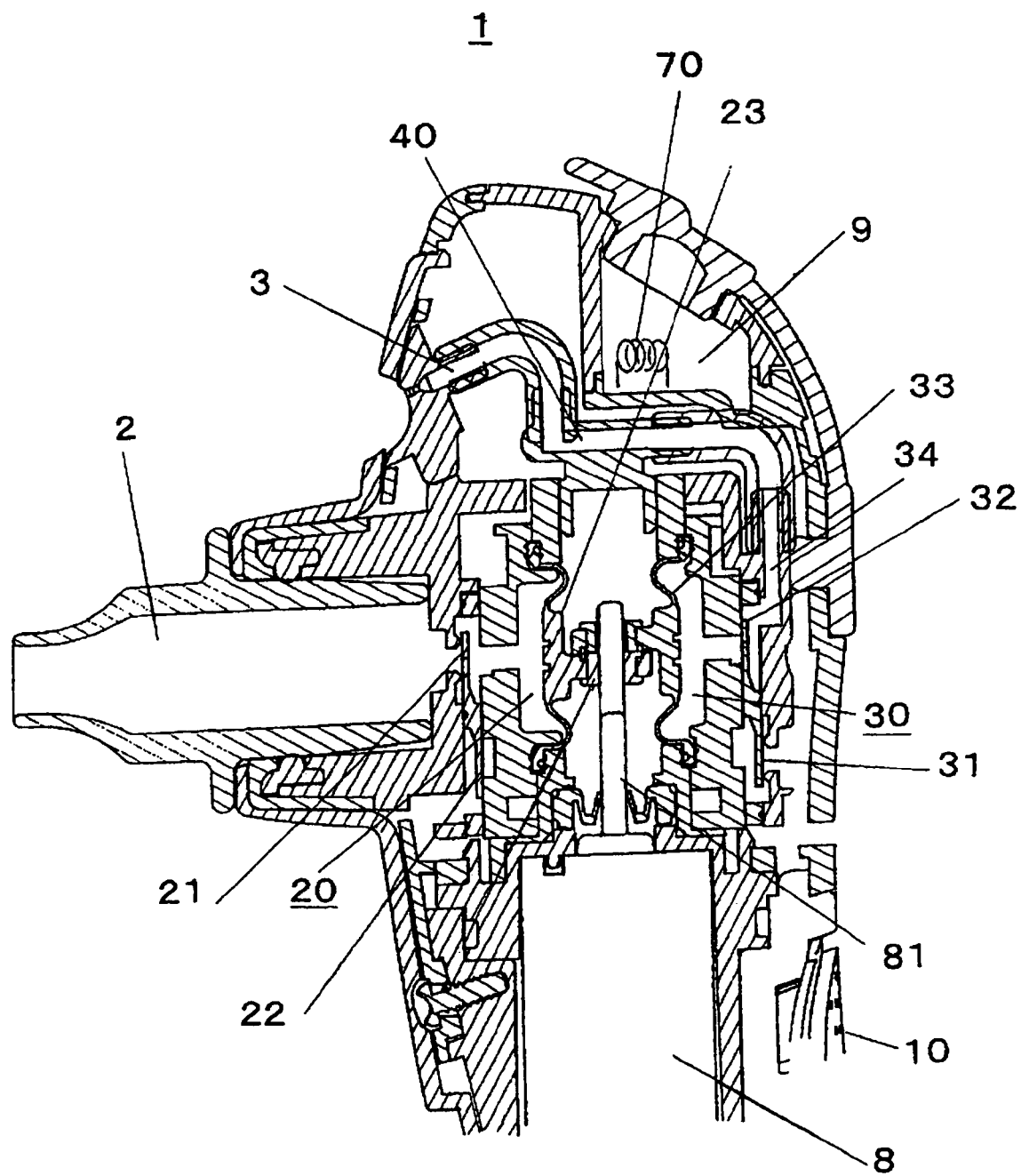
FIG. 3 sets forth an enlarged cross sectional view of parts located above a drive motor shown in FIG. 2.

Referring to FIG. 3, there is provided an enlarged cross sectional view of parts of the skin care device 1 located above the drive motor 8 shown in FIG. 2. The suction pump 20 includes a suction valve 21 for opening or closing a rear end of the suction nozzle 2; an exhaust valve 22 formed as one body with the suction valve 21 to perform on-off operations reverse to those of the suction valve 21; an elastic body (diaphragm) 23 to be deformed to change the volume of the inner space of the suction pump 20; and so forth.

If the elastic body 23 is deformed in a direction that increases the volume of the inner space of the suction pump 20 while a suction port at a front end of the suction nozzle 2 is opened, the suction valve 21 is opened while closing the exhaust valve 22 to thereby take in air from the suction port of the suction nozzle 2. On the contrary, if the elastic body 23 is deformed in a direction that reduces the volume of the inner space of the suction pump 20, the suction valve 21 is closed while opening the exhaust valve 22, so that the air inside the suction pump 20 is discharged from an air outlet.

On the other hand, if the elastic body 23 is deformed in the direction that increases the volume of the inner space of the suction pump 20 while the suction port at the front end of the suction nozzle 2 is in contact with the skin, the suction valve 21 is opened while closing the exhaust valve 22, so that the inner spaces of the suction nozzle 2 and the suction pump 20 are communicated with each other, while increasing the volume. As a result, the internal pressures of the suction nozzle 2 and the suction pump 20 are reduced. Then, if the elastic body 23 is deformed in the opposite direction and reduces the volume of the inner space of the suction pump 20, the suction valve 21 is closed, so that the inner space of the suction nozzle 2 is closed as well while maintaining the internal pressure of the suction nozzle 2. Meanwhile, if the exhaust valve 22 is opened, the air inside the suction pump 20 is discharged through the air outlet, so that the internal pressure of the suction pump 20 is made equal to that of the exterior air. If such alternate deformations of the elastic body 23 are repeated, the internal pressure of the suction nozzle 2 is reduced gradually, generating a suction force. As a result, skin impurities can be removed from the skin.

Similarly, the liquid supply pump 30 also includes a suction valve 31 communicating with the outside of the liquid supply pump 30 to suction the exterior air; an exhaust valve 32 formed as one body with the suction valve 31 to perform on-off operations reverse to those of the suction valve 31; an elastic body 33 to be deformed to change the volume of the inner space of the liquid supply pump 30; and so forth. An exhaust port 34 of the liquid supply pump 30 is connected to an ejection port of the mist nozzle 3 for ejecting a mist of liquid, to thereby send the air suctioned by the suction valve 31 to the mist nozzle 3 via an air exhaust conduit 40. The mist nozzle 3 generates a mist of liquid from the Venturi effect.

Figure 4:
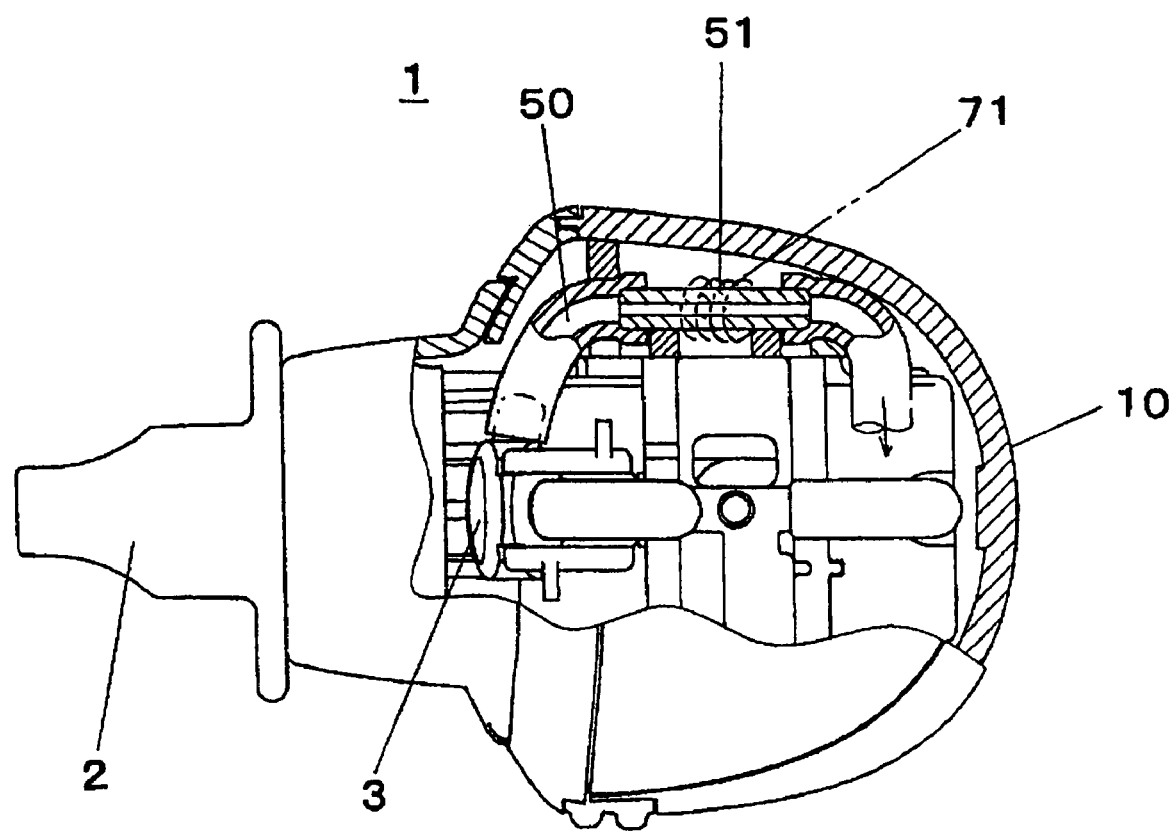
FIG. 4 depicts a plan sectional view illustrating a configuration of a flow rate regulation unit in accordance with the preferred embodiment of the present invention.

A flow rate regulation unit for spraying a small quantity of liquid from the mist nozzle 3 will now be described in detail. In accordance with the preferred embodiment of the present invention, a resistor element for generating a resistance against a negative pressure generated at a liquid supply hole of the mist nozzle 3 is installed between the tank 9 and the mist nozzle 3 in order to reduce the feed rate of the liquid per unit time. Specifically, by forming a part of a conduit 50 for connecting the tank 9 and the mist nozzle 3 with a pipe 51 having a cross sectional area, e.g., a diameter smaller than that of the conduit 50 (hereinafter referred to as a smaller-diameter pipe 51), as shown in FIG. 4, a high level of conduit resistance is generated when the liquid passes through the pipe 51, resulting in a reduction in the flow rate of the liquid. The pipe 51 is preferably made up of a metal, such as stainless steel, to make a rigid body. By using such a smaller-diameter pipe 51, the structure of the flow rate regulation unit can be simplified and an increase in costs can be minimized.

Figure 5A:
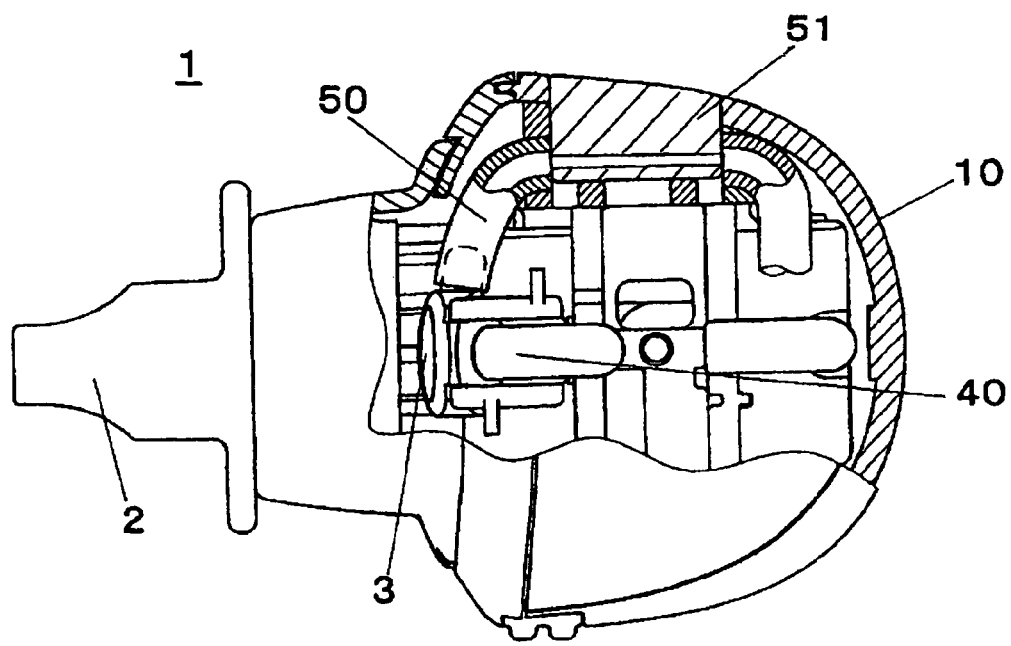
Figure 5B:
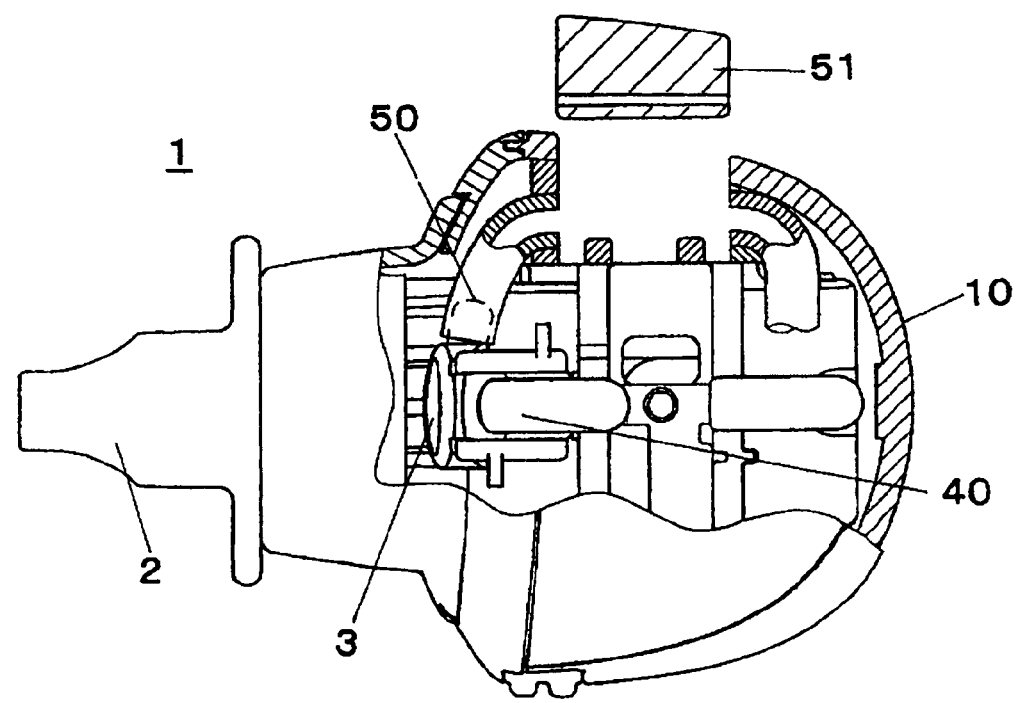
FIG. 5B presents a plan sectional view showing the cartridge of the flow rate regulation unit separated from the skin care device.

Moreover, it is preferable to design the pipe 51 to be of a cartridge type capable of being separated form a main body of the skin care device 1, as shown in FIGS. 5A and 5B. By allowing the smaller-diameter pipe 51 to be detached from the main body, it becomes possible to eliminate dust particles accumulated inside the pipe 51. Furthermore, by providing a plurality of cartridges of pipes 51 having different diameters, the ejection amount of liquid can be adjusted depending on the user's preference.

Figure 6:
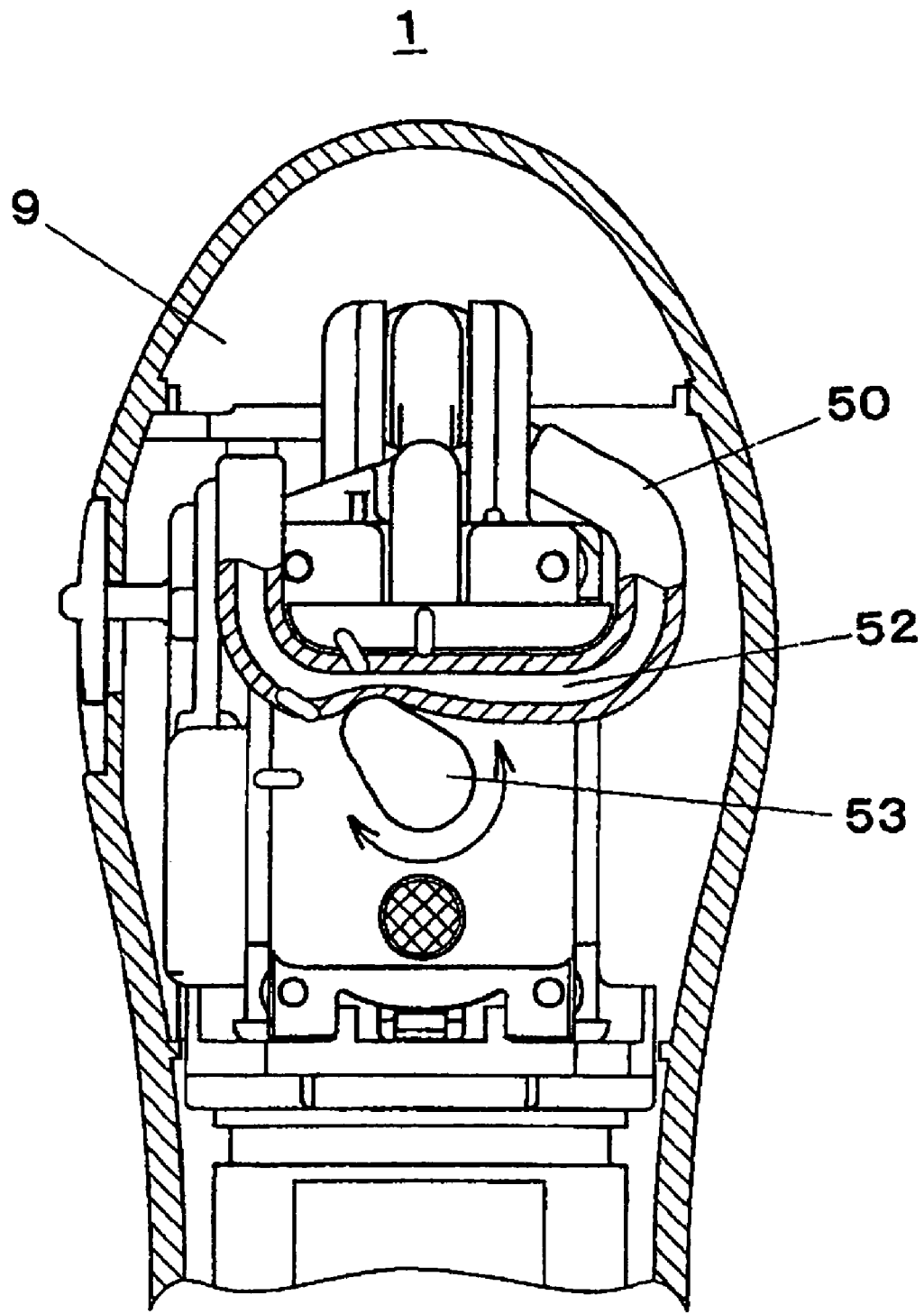
FIG. 6 is a plan sectional view showing another configuration of the flow rate regulation unit.

As shown in FIG. 6, the flow rate regulation unit can be configured to have a resilient tube 52 formed of a resilient material such as rubber and a contact member 53 to be brought into contact with the tube 52 to change (reduce) the cross sectional area of the tube 52. Together with such a configuration, it is also possible to design a part of the conduit 50 to be narrower than the other part thereof, to thereby generate a conduit resistance. Under such configurations, the amount of liquid sprayed from the mist nozzle 3 can be reduced. Further, by allowing the contact member 53 to rotate while changing the cross sectional area of the tube 52 depending on a rotational position thereof, the ejection amount of liquid can be adjusted according to the user's preference.

Figure 7:
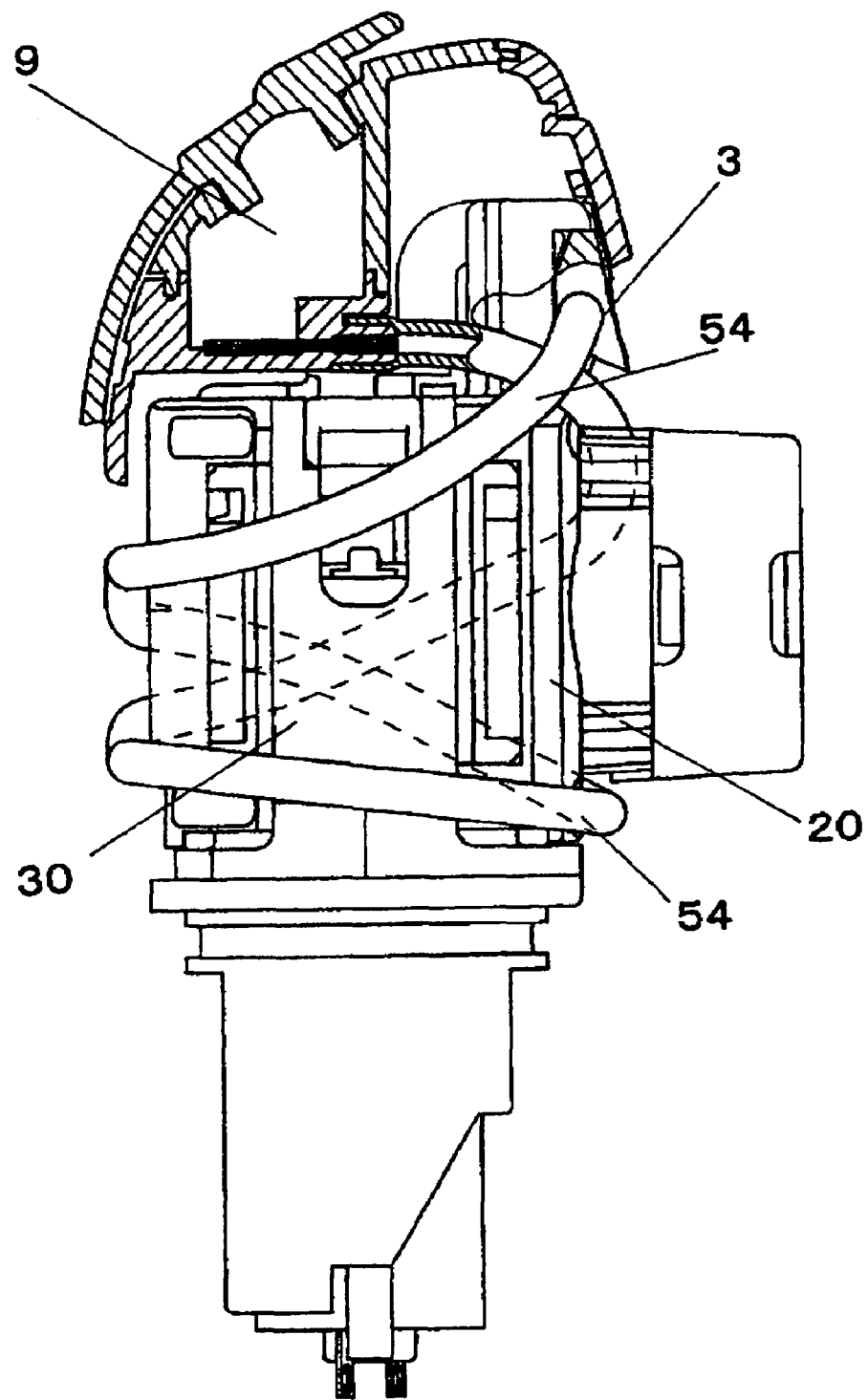
FIG. 7 presents a plan sectional view showing still another configuration of the flow rate regulation unit.

In the above configuration where the conduit resistance is generated by reducing the inner diameter of a part of the conduit 50 between the tank 9 and the mist nozzle 3, there occurs a problem that the conduit 50 may be clogged with foreign substances in case the foreign substances enters the conduit 50, stopping the spraying of the liquid from the mist nozzle 3. For the reason, it is also preferable to elongate the conduit 50 between the tank 9 and the mist nozzle 3, as shown in FIG. 7, as a means to generate a conduit resistance. In such a case, though the size reduction of the skin care device 1 may become difficult because of the long conduit 50, the inner diameter of the conduit 50 can be made substantially uniform, so that the conduit 50 can be prevented from being clogged with foreign substances. Furthermore, by employing a tube 54 as the conduit 50 and arranging the tube 54 on the outer peripheral portions of the suction pump 20 and the liquid supply pump 30 in a spiral shape, an effective use of the inner space of the housing 10 of the skin care device 1 is enabled, which has an effect of preventing the size increase of the skin care device 1.

Figure 8:
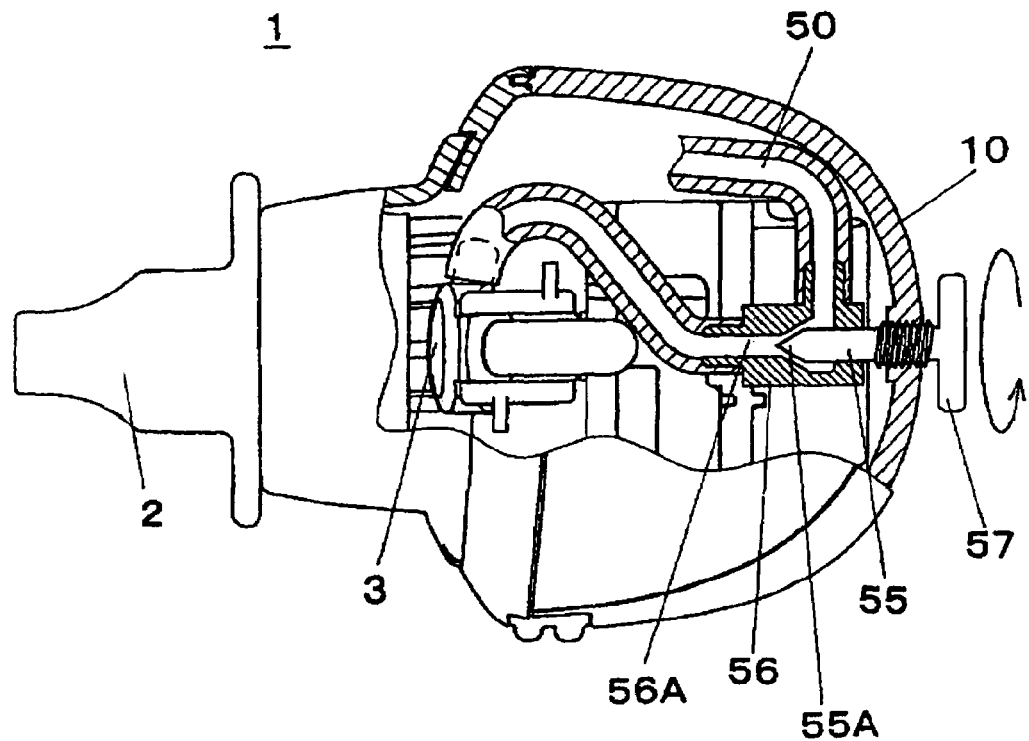
FIG. 8 sets forth a plan sectional view showing still another configuration of the flow rate regulation unit.

In a modification shown in FIG. 8, a pointed pin 55, whose front end is of a conic shape, is projected into a conduit 50 connected between the tank 9 and the suction nozzle 3, to thereby generate a conduit resistance. Further, by varying the projecting degree of the pin 55, the conduit resistance can be changed. As shown in FIG. 8, a block 56 in which the conduit 50 is bent at an approximately right angle is installed on the conduit 50, and the pin 55 is moved by a screwing mechanism 57 in parallel to a conduit 56A which is one of the two portions of the conduit 50 that form the right angle. An inner peripheral surface of the conduit 56A that faces the pin 55 is formed in an approximately conic shape, and a gap between a substantially conic portion 55A at the front end of the pin 55 and the conduit 56A is varied depending on the position of the pin 55. Thus, with the employment of such a configuration, it becomes possible to generate and control the conduit resistance. Since the screwing mechanism 57 can be maneuvered from the outside of the housing 10 and the gap between the conduit 56A and the pin 55 is varied by controlling the screwing mechanism 57, the liquid ejection amount can be controlled according to user preference.

Figure 9:
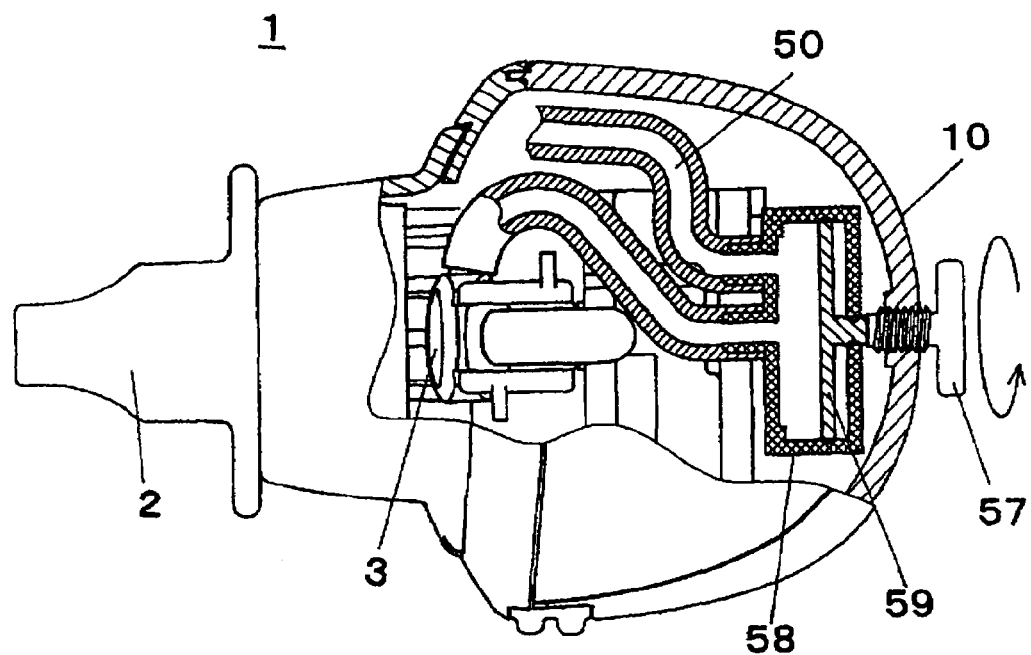
FIG. 9 provides a plan sectional view showing still another configuration of the flow rate regulation unit.

In case of a modification illustrated in FIG. 9, a conduit resistance is generated by installing a liquid storage 58 within a conduit 50 connected between the tank 9 and the suction nozzle 3, and the conduit resistance is changed by varying the inner volume of the liquid storage 58. Further, incorporated in the liquid storage 58 is a partition 59 capable of making parallel movements in a predetermined direction by a screwing mechanism 57. The screwing mechanism can be maneuvered from the outside of the housing 10, and the position of the partition 59 is changed by controlling the screwing mechanism 57, resulting in variation of the inner volume of the liquid storage 58. Accordingly, it becomes possible to vary the liquid ejection amount according to user preference.

In general, as the temperature of the liquid ejected from the suction nozzle increases, the cleaning efficiency of skin impurities is improved, for pores would dilate or sebum is made softer with the temperature rise. Therefore, it is preferable to install a heater 70 inside the tank 9, as illustrated in FIG. 3. By providing the heater 70 within the tank 9, the liquid can be supplied with its temperature increased before being sprayed. Alternatively, it is also possible to install a heater 71 on the conduit 50 connected between the tank 9 and the suction nozzle 3, as shown in FIG. 4. In case of the example shown in FIG. 4, since the heater 71 is disposed on the outer peripheral portion of the pipe 51 formed of a metal, the liquid can be heated efficiently in a short period of time.

Figure 10:
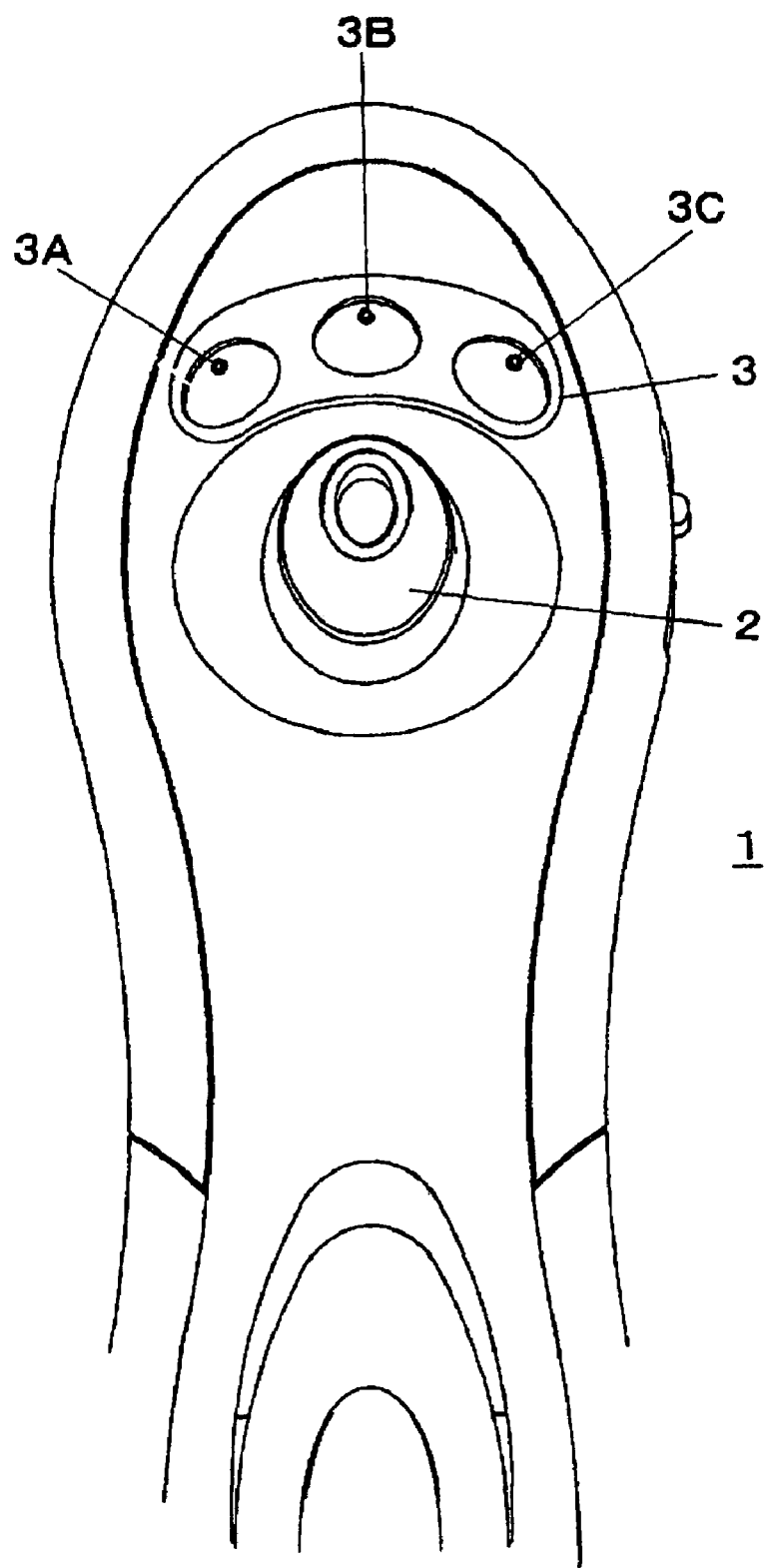
FIG. 10 is a front view showing a configuration with a mist nozzle provided with a plurality of mist ejection holes.
Figure 11:
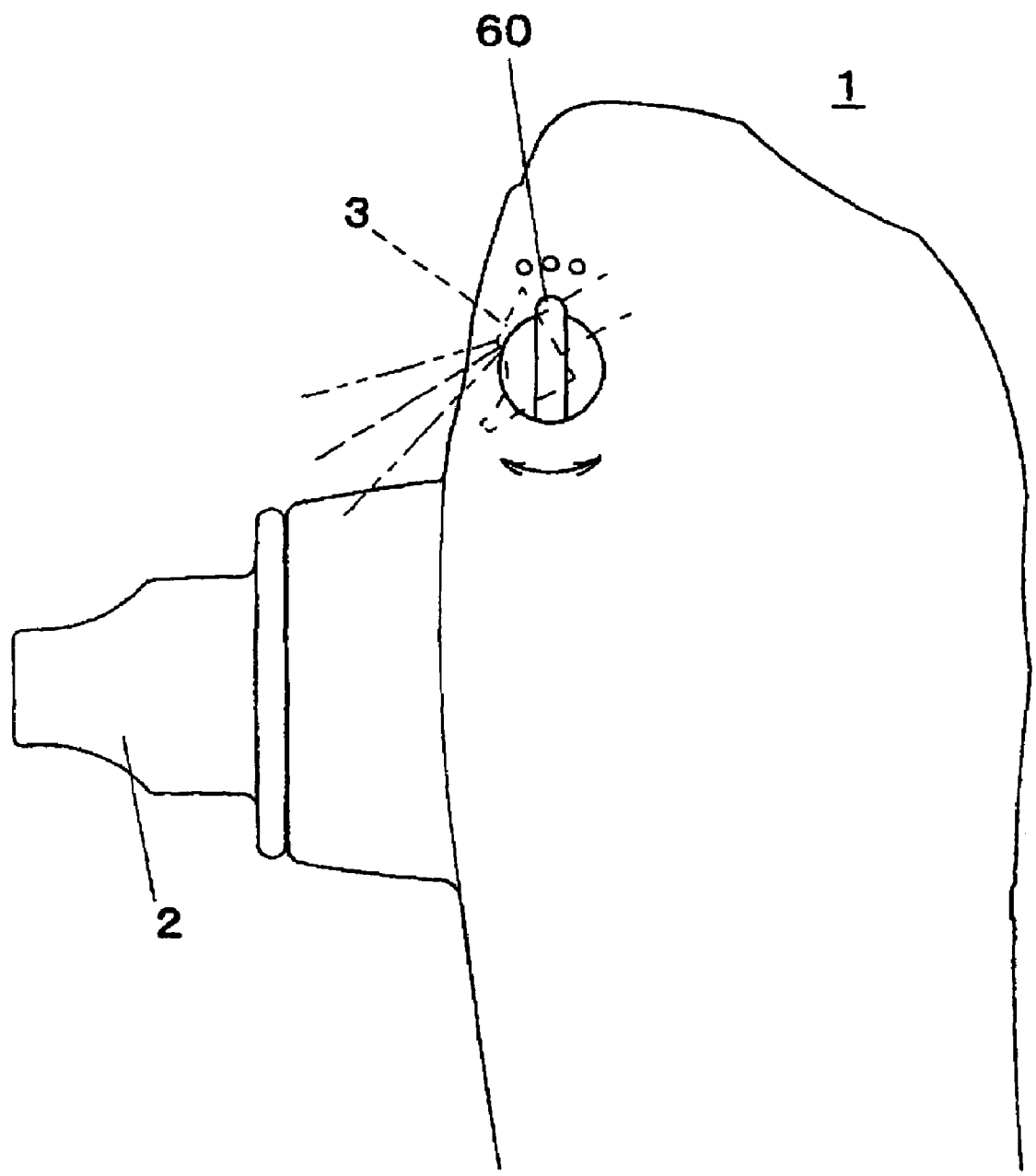
FIG. 11 sets forth a side view of the skin care device provided with a mist ejection angle control device for controlling a mist spray angle of a mist nozzle.

The liquid ejected from the mist nozzle 3 should be present at the interface between the suction port of the suction nozzle 2 and the skin. Thus, it is preferable to dispose the mist nozzle 3 as close to the suction nozzle 2 as possible. However, since the suction pump 20 and the liquid supply pump 30 should be disposed in a limited space, the mist nozzle 3 cannot always be positioned in the vicinity of the suction nozzle 2. Thus, by providing a plurality of mist ejection holes, for example, 3A, 3B and 3C as shown in FIG. 10, which are oriented in different spraying directions, respectively, a uniform supply of liquid to the vicinities of the suction port of the suction nozzle 2 can be realized, and a firm contact between the suction port of the suction nozzle 2 and the skin can be further enhanced. Alternatively, it is also possible to eject the mist of the liquid to a desired position by using a mist ejection angle control device 60 for controlling the mist ejection angle of the mist nozzle 3, as shown in FIG. 11.

Further, in case the amount of the liquid supplied from the mist nozzle 3 to the skin is excessively great, the liquid would drip down the skin of the user, making the user feel unpleasant. In case the liquid amount is too small, on the other hand, a sufficient contact between the suction nozzle 2 and the skin may not be obtained and sufficient sebum removing efficiency may not be attained, either, because it becomes difficult for the suction nozzle 2 to slide on the surface of the skin. Accordingly, the sprayed amount of the liquid needs to be such that it does not cause a discomfort to the user while facilitating the firm contact between the suction nozzle 2 and the skin and allowing the suction nozzle 2 to be slid easily. For example, the ejection amount is preferably set to range from about 0.2 ml/min to about 0.7 ml/min.

While the invention has been shown and described with respect to the preferred embodiments, it will be understood by those skilled in the art that various changes and modifications may be made without departing from the spirit and scope of the invention as defined in the following claims.

What is claimed is:

1. A skin care device comprising:
    a suction nozzle to be brought into contact with skin to suction sebum or other impurities therefrom;
    a suction pump for generating a suction force of the suction nozzle;
    a mist nozzle installed near the suction nozzle, for ejecting a mist of liquid;
    a tank for storing therein a liquid to be supplied to the mist nozzle;
    a liquid supply pump for supplying the liquid to the mist nozzle from the tank;
    a drive motor for driving the suction pump and the liquid supply pump at the same time; and
    a liquid amount control unit for controlling an amount of the liquid ejected from the mist nozzle,
    wherein the suction pump and the liquid supply pump face each other with a rotating shaft interposed therebetween, the rotating shaft being provided on the drive motor.

2. The device of claim 1, wherein the liquid amount control unit is a flow rate regulation device disposed between the tank and the mist nozzle.

3. The device of claim 2, wherein the flow rate regulation device includes a pipe formed at a conduit connected between the tank and the mist nozzle, the pipe having a cross sectional area smaller than that of the conduit.

4. The device of claim 2, wherein the flow rate regulation device is detachable from the skin care device, the flow rate regulation device being of a cartridge type.

5. The device of claim 2, wherein the flow rate regulation device is formed of a resilient tube.

6. The device of claim 2, wherein the flow rate regulation device includes a tube and a contact member to be brought into contact with the tube to change a cross sectional area of the tube.

7. The device of claim 5, wherein the tube is disposed on outer peripheral portions of the suction pump and the liquid supply pump in a spiral shape.

8. The device of claim 2, wherein the flow rate regulation device is a pin projected into a conduit connected between the tank and the mist nozzle and a projecting amount of the pin is controllable from the outside of a housing of the skin care device.

9. The device of claim 2, wherein the flow rate regulation device is a liquid storage disposed in a conduit connected between the tank and the mist nozzle and an inner volume of the liquid storage is controllable from the outside of a housing of the skin care device.

10. The device of claim 2, wherein a heater is installed near a conduit connected between the tank and the mist nozzle.

11. The device of claim 2, wherein a heater is installed inside the tank.

12. The device of claim 2, wherein the mist nozzle is provided with a plurality of mist ejection holes oriented in different ejecting directions, respectively.

13. The device of claim 2, further comprising a mist ejection angle control device for controlling a mist ejection angle of the mist nozzle.

14. The device of claim 2, wherein the ejection amount of the liquid ranges from about 0.2 ml/mm to about 0.7 ml/mm.

* * * * *